United States Patent [19]

Asada et al.

[11] 4,024,252
[45] May 17, 1977

[54] 2-(5-ETHYL-6-BROMOTHIAZOLO[3,2-B]-5-TRIAZOLYL)THIOPHOSPHONATE ESTERS, COMPOSITIONS AND METHOD OF USE

[75] Inventors: Mitsuo Asada, Hiratsuka; Meiki Ando; Michihiko Matsuda, both of Oiso; Tomio Yamada; Hitoshi Watanabe, both of Hiratsuka; Saburo Kano; Osami Nomura, both of Odawara, all of Japan

[73] Assignee: Nippon Soda Company Limited, Tokyo, Japan

[22] Filed: June 19, 1975

[21] Appl. No.: 588,617

Related U.S. Application Data

[63] Continuation-in-part of Ser. No. 386,020, Aug. 6, 1973, abandoned, which is a continuation-in-part of Ser. No. 319,490, Sept. 9, 1975, Pat. No. 3,904,639.

[30] Foreign Application Priority Data

Apr. 7, 1973  Japan .............................. 48-39714

[52] U.S. Cl. .................. 424/200; 260/306.7 T
[51] Int. Cl.² .......................................... A01N 9/36
[58] Field of Search ............. 260/306.7 T; 424/200

[56] References Cited

UNITED STATES PATENTS

| | | | |
|---|---|---|---|
| 3,682,943 | 8/1972 | Hoffmann et al. | 260/306.7 E |
| 3,904,639 | 9/1975 | Kano et al. | 260/306.7 E |
| 3,948,926 | 4/1976 | Kano et al. | 424/200 |
| 3,957,977 | 5/1976 | Hoffmann et al. | 260/306.7 R |
| 3,970,751 | 7/1976 | Kano et al. | 424/200 |

*Primary Examiner*—Donald G. Daus
*Assistant Examiner*—David E. Wheeler
*Attorney, Agent, or Firm*—George B. Oujevolk

[57] ABSTRACT

A compound of the formula

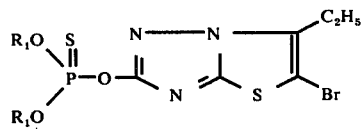

wherein $R_1$ is alkyl having 1 to 3 carbon atoms; is useful as insecticide.

8 Claims, No Drawings

2-(5-ETHYL-6-BROMOTHIAZOLO[3,2-B]-S-TRIAZOLYL)THIOPHOSPHONATE ESTERS, COMPOSITIONS AND METHOD OF USE

This application is a continuation-in-part of U.S. Pat. application No. 386,020 filed Aug, 6, 1973 now abandoned. U.S. Pat. Application No. 386,020 in turn is a continuation-in-part of U.S. Pat. Application Ser. No. 319,490 filed Sept. 9, 1975 now U.S. Pat. No. 3,,904,639. This application is also related to U.S. Pat. No. 3,948,926 which is a division of U.S. Pat. Application No. 386,020.

DETAILED DESCRIPTION OF THE INVENTION

This invention relates to novel thiazolotriazolylphosphonothioates and to a process for the preparation of the same. Further, the invention relates to insecticidal and acaricidal compositions containing one or more of said novel compounds and further includes methods for combatting insects and mites with same compounds.

A number of organo phosphate insecticides have been used for the control of many injurious insects and certain materials are known to be effective. However, many of these synthetic insecticides and acaracides have a strong acute toxicity for human, warm-blooded animals and fishes, and have a long residual toxicity for cultivation plants and live-stocks.

On the other hand, phytophagous mites give the greatest damage to plants and, not to speak of orchard tree, any crop free from mite damage is scarcely found. Its damage is very large and a large sum of extermination expense is used annually. Further, some insects and mites having resistance against the currently employing insecticides and acaricides appear recently. Therefore, it becomes a matter of importance to control the insects and the mites. Accordingly, development of novel, effective insecticides and acaricides are intensively desired in order to control these insects and mites.

The inventors have discovered that the compounds of this invention have superior insecticidal and acaricidal activities for sanitary insect pest, plant insect pest and plant parasitic mite.

The novel compounds of this invention are characterized by the following formula:

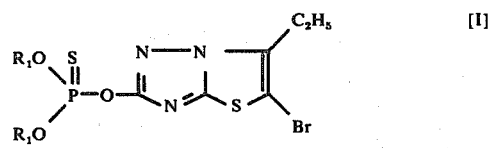

wherein $R_1$ is alkyl having 1 to 3 carbon atoms.

Especially preferred for use because of its low mammal toxicity and insecticidal effectiveness is;

O,O-diethyl 2-(5-ethyl-6-bromothiazolo[3,2-b]-s-triazolyl) thionophosphate.

It is one object of the present invention to provide new thiazolotriazolylphosphonothioates, which are useful in the control of insects and mites. It is another object of the present invention that the compounds of the invention have sufficient low phyto-toxicity to use without damaging living plants and extremely low mammal and fish toxicity.

In the Japanese Patent Publication No. 30192/1961 (U.S.P. 3,682,943) it has been shown that O,O-dialkyl-2-thiazolo[3,2-b]-s-triazolylthionophosphates having no substituent at 6 position therein shown are useful as insecticidal and acaricidal compositions.

But inventors synthesized various thiazolotriazolyl-phosphonothioates and tested the biological activity thereof, and have discovered that thiazolotriazolyl-phosphonothioates having at 6 position the substituent such as bromine have strong insecticidal and acaricidal activities and furthermore, these compounds have very low phyto-toxicity, mammalian and fish toxicity.

For example, acute oral toxicity $LD_{50}$ (mouse) of O,O-diethyl-2-(5-methylthiazolo[3,2-b]-s-triazolyl)thionophosphates of Japanese Patent Publication No. 30192/1971 is 33-50 mg/kg, and one of O,O-diethyl-2-(5-ethyl-6-tromothiazolo[3,2-b]-s-triazolyl)thionophosphate of the present invention is 280 mg/kg, so that it can be said a safety agent.

Furthermore, O,O-dialkyl-2-(5-methyl-6-bromo-thiazolo[3,2-b]s-triazolyl)thionophosphates are described as insecticide in German Patent Application No. P 2264162.9 (Ottenlegungsschrift), but said compound has the strong fish and acute oral toxicity as compared with the compound of the present invention.

For example, medium tolerance limit (48 hrs) for carp and acute oral toxicity $LD_{50}$ (mouse) of O,O-diethyl-2-(5-methyl-6-bromothiazolo[3,2-b]-s-triazolyl)thionophosphate is respectively below 0,05 ppm and 150 mg/kg, but ones of O,O-diethyl-2-(5-ethyl-6bromothiazolo[3,2-b]-s-triazolyl)thionophosphate of the present invention is 18.5 ppm and aforesaid 280 mg/kg. Above low toxicities are due to the introduction of ethyl group instead of methyl at 5 position of thiazolyl ring.

The compounds of this invention can be prepared in accordance with the following equation:

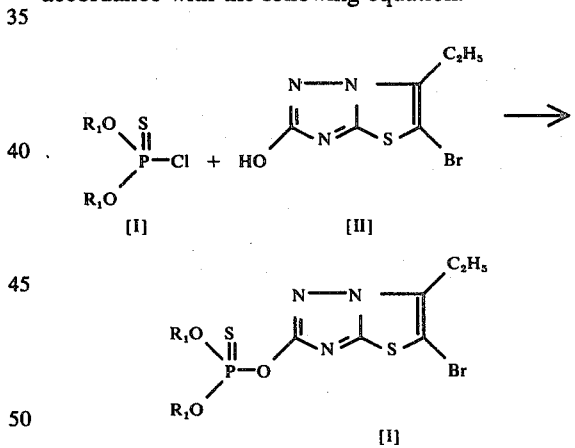

(wherein $R_1$ represent the aforesaid meanings.)

Usually the process for the preparation of the invention is carried out in a proper inert solvent by the use of alkali condensing agents. As an inert solvent, acetone, dioxane, acetonitrile and pyridine have been employed as yet. Using these inert solvents, the compounds of this invention are obtained in low yield such as 5 to 6%.

However, inventors have discovered that the compounds of this invention are obtained in satisfactory high yields such as 50 to 70% when dimethylformamide or dimethylsufoxide are employed as solvents in the presence of potassium carbonate or sodium carbonate as condensing agents.

In practical method the compounds of this invention are prepared through the reaction of O,O-dialkylthiophosphorylchloride with 6-halogenothiazolo[3,2-b]-s- triazol using dimethylformamide or dimethylsulfoxide as solvent in the presence of alkali carbonate as condensing agent, or with alkali metal salts of 6-halogenothiazolo[3,2-b]-s-briazol which are dissolved in the solvent such as dimethylformamide or dimethylsulfoxide. Reaction temperature is 40° – 60° C, preferably 45° – 50° C and the reaction terminates between 4 and 10 hours. After the reaction is terminated, the products are isolated from the reaction mixture by employing the following treatment. The reaction mixture is poured into water after cooling to the room temperature, this water mixture is alkalized by adding dilute sodium hydroxide solution and unreacted starting materials are dissolved in the alkali solution. The crystallized material was obtained by filtration, washed with water and dried, the crude product is obtained as a crystal. The crude product can be purified by recrystallizing from a mixture of ligroin and petroleium ether. The objective product is obtained as white crystal. Untreated starting material can be recovered from the mother liquor acidified with hydrochloric acid solution. The starting material [III] can be prepared in accordance with the following equation:

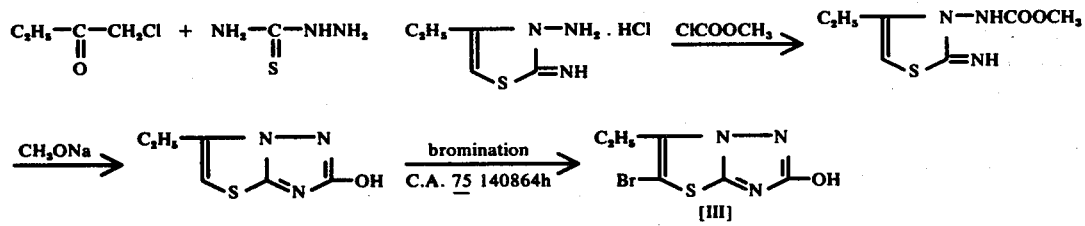

In order to facilitate a clear understanding of the invention, the following preferred specific embodiments are described as illustrative and not as limiting the invention.

EXAMPLE 1

O,O-Dimethyl 2-(5-ethyl-6-bromothiazolo[3,2-b] s-triazolyl) thionophosphate

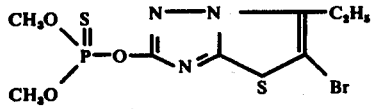

3.1g of 2-hydroxy-5-ethyl-6-bromothiazolo[3,2-b]-s-triazole, 1g of potassium carbonate and 2.1g of O,O-dimethylthionophosphoryl chloride were dissolved in 15 ml of dimethylformamide and heated at 35° – 40° C for 4 hours under agitation. Then the reaction mixture was poured into water and alkalized sodium hydroxide solution to crystallize the reaction product. The crystallized material was gathered by filtration, washed with water and dried. The dried crystal was recrystallized from n-hexane and 3.35g of white needle having a melting point of 55° – 56° C were obtained. The crystal consist of O,O-dimethyl 2-(5-ethyl-6-bromothiazolo[3,2-b]-s-triazolyl) thionophosphate, and the elemental analysis was as follows; Found (%): C 25.63, H 2.75, N 11.00, S 17.21, Br 21.74, P 8.18; calcd. for $C_8H_{11}N_3O_3S_2BrP$(%): C 25.80, H 2.95, N 11.29, S 17.74, Br 21.50, P 8.33.

EXAMPLE 2

O,O-Diethyl 2-(5-ethyl-6-bromothiazolo[3,2-b]-s-triazolyl) thionophosphate

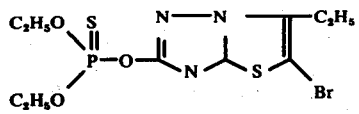

3.1g of 2-hydroxy-5-ethyl-6-bromothiazolo[3,2-b]-s-triazole, 1g of potassium carbonate and 2.32g of O,O-diethylthionophosphoryl chloride were dissolved in 15 ml of dimethylformamide and heated at 40° – 50° C for 4 hours under agitation. By a procedure similar to Example 1, 4.0g of white needle O,O-diethyl 2-(5-ethyl-6-bromothiazolo[3,2-b]-s-triazolyl)thionophosphate having a melting point of 67° – 68° C (ligroin) were obtained. Elemental analysis was as follows; Found(%): C 29.79, H 3.91, N 10.27, S 16.00, Br 20.11, P 7.79, Calcd. for $C_{10}H_{15}N_3O_3S_2BrP$(%): C 30.00, H 3.75, N 10.50, S 16.00, Br 20.00, P 7.75.

EXAMPLE 3

O,O-diisopropyl 2-(5-ethyl-6-bromothiazolo[3,2-b]-s-triazolyl)thionophosphate

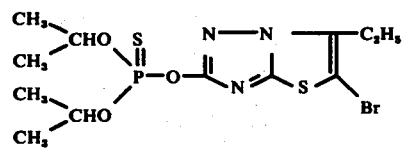

3.1g of 2-hydroxy-5-ethyl-6-bromo[3,2-b]-s-triazole, 1g of potassium carbonate and 2.97g of O,O-diisopropylthionophosphorly chloride were dissolved in 15 ml of dimethylformamide and heated at 40° – 45° C for 3 hours under agitation. By a procedure similar to Example 1, 4.01g of white needle O,O-diisopropyl 2-(5-ethyl-6-bromothiazolo[3,2-b]-s-triazolyl)thionophosphate having a melting point of 50° – 51° C were obtained. Elemental analysis was as follows; Found(%): C 33.70, H 4.71, N 9,82, S 15.00, Br 18.64, P 7.04; Calcd. for $C_{12}H_{19}N_3O_3S_2BrP$(%): C 33.64, H 4.43, N 9.81, S 14.95, Br 18.69, P 7.24.

The method of the present invention comprehends the employment of a liquid or solid composition containing one or more of the present compounds as an active component.

The compound can be used directly without mixing with suitable carriers.

The active ingredient of this invention may be formulated by mixing with suitable carriers in a form generally used in insecticidal and acaricidal compositions such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, xylene, cyclohexane, cyclohexanone, dimethylformamide, dimethylsulfoxide, alcohol, acetone, benzene and others are used. Sometimes surface active agent is added in order to give a homogeneous and stable formulation.

The compounds of this invention can be applied as insecticides and acaricide in any manner recognized by the art. One method for destroying insects and acarids comprises applying to the locus of the insect and acarid infestation, an insecticidal and acaricidal composition comprising an inert carrier and as the essential active ingredient, in a quantity which is toxic to said insects and acarids, a compound of the present invention.

The concentrations of the active ingredients in the insecticidal and acaricidal compositions of this invention vary according to type of formulation and they are, for example, used in a range of 5 – 80 weight percent, preferably 20 – 80 weight percent, in wettable powders, 5 – 70 weight percent, preferably 10 – 50 weight percent, in emulsifiable concentrates, and 0.5 – 20 weight percent, preferably 1 – 10 weight percent in dust formulations.

Furthermore, the composition may be applied as a mixture with other fungicides, insecticides, acaricides, plant growth regulators and herbicides.

Typical insecticidal and acaricidal compositions according to this invention are illustrated by the following examples.

EXAMPLE 4:

Dust Formulation

|  | Parts by weight |
|---|---|
| Product of Example 1 | 4 |
| Talc | 96 |

These are mixed homogeneously and micronized to fine particles. Consequently, dust formulation containing 4% of the active ingredient is obtained. In practical use it is directly applied.

EXAMPLE 5:

Wettable Powder

|  | Parts by weight |
|---|---|
| Product of Example 2 | 30 |
| Higher alcohol sulfonate ester | 7 |
| Diatomaceous earth | 63 |

These are mixed homogeneously and micronized to fine particles. Consequently, wettable powder containing 30% of active ingredient is obtained. In practical use, it is diluted to a certain concentration with water and is sprayed as a suspension.

EXAMPLE 6:

Emulsifiable Concentrate

|  | Parts by weight |
|---|---|
| Product of Example 3 | 40 |
| Xylene | 35 |
| Dimethylformamide | 17 |
| Polyoxyethylene alkylarylether | 8 |
| These are mixed and dissolved. | |

Consequently, emulsifiable concentrate containing 40% of the active ingredient is obtained. In practical use, it is diluted to certain concentration with water and then is sprayed as an emulsion.

In the Example 4 – 6, it is not intended to limit the emulsifiable concentrate, wettable powder, or dust formulation, carriers and solvents to the ones described by way of illustration.

The new compounds of this invention can be used in many ways for the control of insects. Insecticides which are to be used as stomach poisons can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insert breathes. In some cases, the compounds applied to the soil or plant surfaces are taken up by the plant, and the insects are poisoned sustemically.

The above methods of using insecticides are based on the fact that almost all the injury done by insects is a direct or indirect result of their attempts to secure food. Among the insects which can be effectively controlled by the compounds of the present invention are flies, mosquitoes, cockroaches, plant hoppers, rice borers, aphids, scales, leaf roller and other lepidopterous insect pests such as armyworm and tobacco cutworm.

Among the acarids which can be effectively controlled with the compound of the present invention are the desert spider mite, two-spotted spider mite, citrus red mite and Japanese citrus rust mite.

The compounds of the present invention are particularly effective against insects such as tobacco cutworm, rice stem borer, northern house mosquito, smoky brown cockroach and diamondback moth.

The compounds of the present invention possess very superior insectidical and acaricidal activities compared to known compounds.

The superior insecticidal and acaricidal effects of the novel compounds of this invention are clearly illustrated by the following tests.

In these all tests, O,O-diethyl-2-(5-methyl-thiazolo[3,2-b]-s-triazolyl)thionophosphate of the Japanese Patent Publication No. 30192/1971 is compared with the compounds of this invention.

Test 1

Insecticidal Activity against Fly

Fixed concentration of acetone solution containing test compound were prepared.

20 pieces of female adults of house flies (*Musca domestica* Linne) were tested with 1 μl of acetone solution at their thoracie dorsal by microcylinge and kept at a temperature of 25° C and at a humidity of 65%. 24 hours and 48 hours after treatment, dead flies were counted and mortality (%) was calculated. The results were shown in Table 1.

Table 1

| Test Compound | Active compound 0.5γ/a fly | | Active compound 0.25γ/a fly | |
|---|---|---|---|---|
| | 24 hrs. | 48 hrs. | 24 hrs. | 48 hrs. |
| Product of Example 2 | 100 | 100 | 30 | 40 |
| Comparison | 70 | 70 | 0 | 10 |

Table 1-continued

| Test Compound | Active compound 0.5γ/a fly 24 hrs. | 48 hrs. | Active compound 0.25γ/a fly 24 hrs. | 48 hrs. |
|---|---|---|---|---|
| compound* | | | | |

*O,O-diethyl-2-(5-methylthiazolo[3,2-b]-s-triazolyl)thionophosphate

Test 2

Insecticidal Activity against Cabbage armyworm

10 Multigeneration bred armyworms (*Leucania separate* Walker) were used for one experimental zone.

A leaf of corn plant was dipped in an aqueous emulsion of emulsifiable concentrate formulated in similar manner to Example 6 for 30 seconds and air dried. Then the leaf was set an filter paper having 9 cm diameter in a schale. The test insects were inoculated into the dish and the cover was put on it. After 1 day and 3 days from inoculation, dead insects were counted and mortality (%) were calculated. The results were shown in

Table 2

| Test Compound | Concentration 31.3 ppm 1 day | 3 days | Concentration 15.7 ppm 1 day | 3 days | Concentration 7.8 ppm 1 day | 3 days |
|---|---|---|---|---|---|---|
| Product of Example 1 | 100 | 100 | 60 | 100 | 50 | 90 |
| Product of Example 2 | 100 | 100 | 90 | 100 | 60 | 100 |
| Product of Example 3 | 100 | 100 | 60 | 100 | 50 | 90 |
| Comparison Compound* | 70 | 100 | 30 | 80 | 0 | 0 |

Test 3

Test for Control of Mite

About 30 adult female mites of desert spider mite (*Tetranychus desertorum* Banks) laid on main leaves of the potted kidney bean plants grown 7 to 10 days stage after aprouting. One day later, the wounded mites were removed from the plants. The compounds to be tested were sprayed on the plants as water suspension of emulsifiable concentrate prepared by the method of Example 6. After 1 day and 3 days from spraying, dead mites were counted and mortality (%) was calculated. Rating of mortality was recorded as follows:

| Mortality | Rating |
|---|---|
| 100 % | +++ |
| 99 – 90 % | ++ |
| 89 – 50 % | + |
| 50 – 0 % | − |

The results are shown in Table 3.

Table 3

| Test compound | Concentration of Active Ingredient 500 ppm 3 days |
|---|---|
| Product of Example 1 | +++ |
| Product of Example 2 | +++ |
| Comparison Compound* | +++ |

Test 4

Insecticidal Activity against Rice stem borer 20 hatched nymph of Rice stem borer (*Chilo suppressalis* Walker) were inoculated to the potted rice (height: 30 – 40 cm, number: 4/pot). A week after inoculation, 30 ml of fixed concentration of solution containing test compound were sprayed on the rice in which hatched nymph were inhabiting and the pots were kept at the room temperature. A week after spraying, the rice was opened, dead Rice stem borers were counted and mortality (%) was calculated.

The results were shown in Table 4.

Table 4

| Test compound | Concentration 31.3 ppm | Mortality (%) Concentration 15.6 ppm | Concentration 7.8 ppm |
|---|---|---|---|
| Product of Example 2 | 100 | — | 91 |
| Comparison Compound* | 100 | 84 | — |

Test 5

Test for Control of Tobacco cutworm

A leaf of sweet potato was dipped for 30 seconds in an aqueous suspension of a wettable powder diluted to a certain concentration with water and air-dried.

Then the leaf and 5 tobacco cutworms (*Prodenia litura* Fabricius) of 3 stages larva were put into a covered dish.

The test was carried out twice. After 3 days from inoculation, dead insects were counted and mortality (%) was calculated. The results were shown in the Table 5.

Table 5

| Test Compound | Concentration (p.p.m.) | Mortality (%) |
|---|---|---|
| Product of Example 2 | 125 | 100 |
| | 62.5 | 100 |
| | 31.3 | 80 |
| | 15.6 | 60 |
| Comparison Compound | 125 | 100 |
| | 62.5 | 80 |
| | 31.3 | 0 |

Test 6.

Insecticidal Activity against Mosquito

An aqueous suspension of formulated wettable powder were poured in 200 ml beaker and in which 20 northern house mosquito (*Culex pipiens molestus* Forskal) were inoculated. 24 hours after inoculation, dead mosquitos were counted and the results were shown in Table 6.

Table 6

| Test compound | $LC_{50}$ (ppm) |
|---|---|
| $(C_2H_5O)_2-\overset{S}{\underset{\|}{P}}-O-\underset{N}{\overset{N-N}{\underset{S}{\bigvee}}}\overset{C_2H_5}{\underset{Br}{}}$ | 0.003 |
| $(C_2H_5O)_2-\overset{S}{\underset{\|}{P}}-O-\underset{N}{\overset{N-N}{\underset{S}{\bigvee}}}CH_3$ U.S.P. 3682943 | 0.04 |

Toxicity Test 1

Suspension of the test compound in 25% aqueous solution of gum arabic was compulsorily treated to six mice by means of a stomack tube and inspection had been made for 2 weeks.

The results were tabulated below in Table 7.

Table 7

| Test compound | LD$_{50}$ (milligram/kilogram) |
| --- | --- |
| 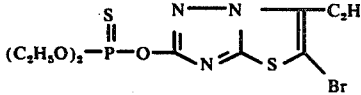 | 280 |
| 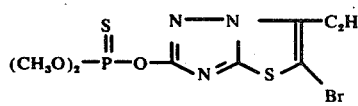 | over 200 |
| 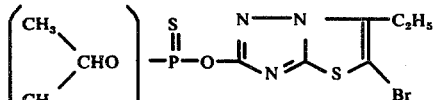 | over 200 |
| 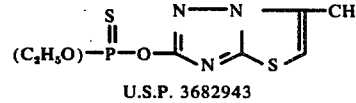 U.S.P. 3682943 | 33 ~ 50 |

Toxicity Test 2

The test compound was dissolved in dimethylformamide and said solution was added to 20 liters of water containing 10 carps (*Cyprinus carpio*) in a fixed concentration.

Dead fish within 48 hours from the addition of test compounds was counted.

The results were shown in Table 8 as medium tolerated limit (TLm).

Table 8

| Test compound | TLm* (ppm) |
| --- | --- |
| 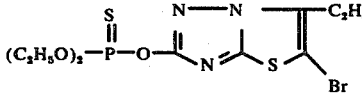 | 18.5 |
| 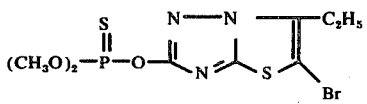 | over 5 |
| 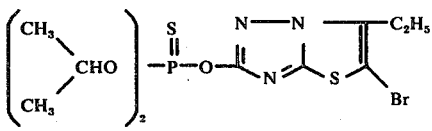 | over 5 |
| 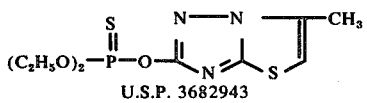 U.S.P. 3682943 | under 0.5 |

*TLm is the concentration of test compound which half the number of fish die.

We claim:
1. An insecticidal composition useful in the combatting of the phytophagous insect, mosquito, rice stem borer, cabbage army worm and fly, consisting essentially of a carrier and an insecticidally effective amount of a compound represented by the formula

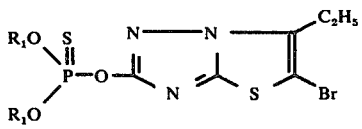

wherein R$_1$ is alkyl having 1 to 3 carbon atoms.

2. A method of combating insects of the phytophagous insect, mosquito, rice stem borer, cabbage army worm, and fly variety which comprises applying to the insect an insecticidally effective amount of the formula

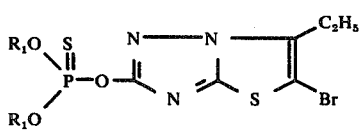

wherein R$_1$ is alkyl having 1 to 3 carbon atoms.

3. A method according to claim 2 wherein R$_1$ is ethyl.
4. A method according to claim 2 where in R$_1$ is methyl.
5. A method according to claim 2 wherein R$_1$ is isopropyl.
6. A composition according to claim 1 in which R$_1$ is ethyl.
7. A composition according to claim 1 in which R$_1$ is methyl.
8. A composition according to claim 1 in which R$_1$ is isopropyl.

* * * * *